(12) United States Patent
Evans et al.

(10) Patent No.: US 6,255,432 B1
(45) Date of Patent: Jul. 3, 2001

(54) HOT MELT INK JET VEHICLES

(75) Inventors: Philippa Catherine Evans, West Glamorgan; Stephen Anthony Hall, South Glamorgan, both of (GB)

(73) Assignee: Coates Brothers PLC, Kent (GB)

( * ) Notice: Subject to any disclaimer, the term of this patent is extended or adjusted under 35 U.S.C. 154(b) by 0 days.

(21) Appl. No.: 09/043,799

(22) PCT Filed: Sep. 27, 1996

(86) PCT No.: PCT/GB96/02399

§ 371 Date: Jul. 15, 1998

§ 102(e) Date: Jul. 15, 1998

(87) PCT Pub. No.: WO97/12003

PCT Pub. Date: Apr. 3, 1997

(30) Foreign Application Priority Data

Sep. 27, 1995 (GB) .................................................. 9519646

(51) Int. Cl.$^7$ ..................................................... C08G 18/08
(52) U.S. Cl. ..................... 528/49; 106/31.13; 106/31.43; 528/68; 528/69; 528/85
(58) Field of Search .................................. 528/49, 68, 69, 528/85; 106/31.13, 31.43

(56) References Cited

FOREIGN PATENT DOCUMENTS 9414902   7/1994  (WO) .

OTHER PUBLICATIONS

Database WPI, Section Ch, Week 9244, Derwent Publications Ltd., London, GB; Class G05, AN 92–360947 XP002022532 & JP A 04 261 477 (Canon KK) (Sep. 17, 1992) see abstract.

Database WPI, Section Ch, Week 9233, Derwent Publications Ltd., London, GB; Class A28, AN 92–272925 XP002022533 & JP A 04 185 677 (Sanyo Chem Ind Ltd) (Jul. 2, 1992) see abstract.

*Primary Examiner*—John Cooney
(74) *Attorney, Agent, or Firm*—Ostrolenk, Faber, Gerb & Soffen, LLP

(57) ABSTRACT

A hot melt inkjet vehicle is obtained by reacting a mono- or diisocyanate with functional amide materials. The functional amides are the reaction products of hydroxy functional primary and/or secondary amines and/or diprimary diamines together with a monofuntional carboxylic acid and/or hydroxy carboxylic acid and/or a difunctional carboxylic acid.

17 Claims, No Drawings

HOT MELT INK JET VEHICLES

The present invention relates to the formulation of hot melt ink jet base materials (hereinafter referred to as "ink jet vehicles") with a view to improving their compatibility with viscosity modifying additives.

Ink jet printing generally comprises forming a patterned array of droplets of an ink upon a substrate to form the desired indicia on the substrate. In a hot melt ink jet printing process, the ink is one which is normally solid at ambient temperatures and which is applied to the substrate in molten form so that the droplets solidify on cooling on the substrate.

Typically, the ink employed in hot melt ink jet printing comprises a fusible carrier together with a colourant, i.e. a pigment or dyestuff. Suitable materials for use as or in the vehicles for inks for hot melt ink jet printing (hereinafter, simply, "hot melt inks") should be relatively hard and non-tacky at ambient temperatures whilst being capable of melted to form inks. Suitably, they have a melting point of at least 65° C.

Patent Specification WO 94/14902 describes the use of certain urethane oligomers as hot melt ink vehicles. These oligomers are the reaction products of diisocyanates with a monohydric alcohol component, optionally followed by another monohydric component or a dihydric alcohol component followed by a monohydric alcohol component. These materials have melting points in excess of 65° C., low melt viscosities and good colour and viscosity stabilities at elevated temperatures. However, they are compatible with only a limited number of viscosity modifiers. This drawback may limit the range of applications of such materials, where certain specific properties, not possessed by the materials alone, are required.

A new class of hot melt ink jet vehicles has now been devised, which overcomes the aforementioned limitation in the range of possible applications. Thus, in accordance with the present invention, there may be used as hot melt ink jet vehicles, the reaction products of a mono- or diisocyanate and one or more functional amides. The present invention also provides the use of a urea or urethane compound having a melting point greater than 65° C., as a hot melt ink jet vehicle, the urea or urethane compound being the reaction product of a mono- or diisocyanate and a functional amide.

According to one embodiment of the present invention, there is provided a material suitable for use in a hot melt ink, the material being obtainable by reacting a mono- or diisocyanate with one or more functional amide materials which are the reaction products of:

(a) (i) one or more hydroxy functional primary or secondary amines; or
    (ii) one or more diprimary diamines; or
    (iii) a mixture of components (i) and (ii); and
(b) a monofunctional carboxylic acid, a hydroxy carboxylic acid or difunctional carboxylic acid or a mixture of any two or more thereof.

Very preferably, materials according to the present invention have a a melting point in excess of 65° C. They also have good thermal colour and viscosity stability as well as improved compatibility with common viscosity modifiers.

More specifically, preferred materials according to the present invention may be produced by reacting a mono- or di-functional aliphatic or aromatic isocyanate with an at least stoichiometric amount of:

(i) the reaction product of one equivalent of a diprimary diamine component with one equivalent of a monocarboxylic acid and one equivalent of a hydroxy functional monocarboxylic acid;

(ii) the reaction product of one equivalent of a diprimary diamine component with one equivalent of a monocarboxylic acid;

(iii) the reaction product of one equivalent of a primary monoamine with hydroxy functionality, with one equivalent of a monocarboxylic acid; or (iv) the reaction products (i) or (ii), but where an equivalent of acid functionality is made up of a proportion of monocarboxylic acid, dicarboxylic acid and/or hydroxy functional monocarboxylic acids.

The amides produced by the reactions described above may be hydroxy or amine functional, depending on the proportions and type of reagent used. Thus the reaction products obtained from these amides and the isocyanate materials will be urethane or urea compounds depending on whether the isocyanate groups react with hydroxy or amine groups respectively.

As noted above, it is greatly preferred that materials according to the present invention (hereinafter referred to as urethane-amides or urea-amides) have a melting point greater than 65° C. (as determined by the ball and ring method). It should be noted that not all materials obtainable by the processes outlined above have melting points greater than 65° C. Our experiments have shown that there is a wide range of melting points and that attempts to predict the melting point, by taking molecular weight or component reagents into account, are fruitless. However, of course it is simple to measure the melting point once the material has been made, by simple routine and trial.

Suitable isocyanates for use in the preparation of the urethane- and urea-amides include octadecylmonoisocyanate, toluene diisocyanate, diphenylmethane-4,4'-diisocyanate (MDI), hexamethylene-1,6-diisocyanate, naphthalene-1,5-diisocyanate, 3,3'-dimethyl-4,4'-biphenyl diisocyanate, isophorone diisocyanate, trimethylhexamethylene diisocyanate and tetramethylene xylene diisocyanate. Of these isocyanates the aliphatic materials are generally preferred to the aromatic ones for reasons of heat and viscosity stability. In particular isophorone diisocyanate, trimethylhexamethylene diisocyanate and octadecyl monoisocyanate have been found to be particularly suitable for this application.

Diprimary diamines which may be used to produce the amides for isocyanate adduction, including ethylene diamine, neopentane diamine, 2,4,4-trimethylhexandiamine, 2-butyl-2-ethyl 1,5 pentane diamine, 1,3-diaminopentane, isophorone diamine and 2 methyl 1,5 pentamethylene diamine. Hydroxy functional primary and secondary amines which may be used are ethanolamine, diethanolamine and n-methyl diethanolamine. In particular ethylene diamine is suitable in this type of formulation.

Monocarboxylic acids which are suitable for this application are stearic acid, acetic acid, 3,5,5-trimethylhexanoic acid, decanoic acid, propanoic, acid 2,2 dimethyl propionic acid, isooctanoic acid, isoheptanoic acid, isobutynic acid, or isodecanoic acid. Stearic and 3,5,5-trimethylhexanoic acids have proved particularly suitable in this application. Dimer acids are suitable difunctional carboxylic acids.

Hydroxy functional monocarboxylic acids which may be used include 12-hydroxy stearic acid, 12-hydroxydodecanoic acid, 2-hydroxyhexanoic acid, 16-hydroxyhexadecanoic acid and 2-hydroxyisobutyric acid. 12-hydroxystearic acid and 12-hydroxydodecanoic acid have proved particularly useful in this application.

The amide components of the hot melt ink vehicle typically have melting points (ball and ring) of >50° C. and viscosities <200 centipoise at 125° C.

The condensation reaction used to produce the amide component of the urethane- and urea-amides proceeds without need of a catalyst. The reaction of the amide with the isocyanate component may also be carried out without a catalyst, but catalysts such as dibutyl tin dilaurate and stannous octoate may be used to ensure full reaction of the isocyanate fraction.

The final average molecular weight of the urethane- or urea-amides is typically from 400 to 2000, preferably from 800 to 1400. These materials having melting points of from room temperature (e.g. 20° C.) to 130° C. and melt viscosities of from 10 to 800 centipoise at 125° C.

For some applications of hot melt inks it is advantageous if the urethane- or urea-amides are transparent. As with the melting points described previously, it is impossible to predict which particular mix of reagents will produce a clear product. Again determination of suitable materials is by simple trial and experiment. Similarly, the viscosity of the materials at elevated temperatures is not easily predicted, materials with viscosities lower than 200 centipoise at 125° C. proving of greatest use for this type of application, with materials with viscosities less than 50 centipoise at 125° C. being of particular interest.

The urea- and urethane-amides of this invention are used as vehicles, or as a components of vehicles, of hot melt ink jet inks. As well as the aforementioned urea- and urethane-amides these inks will also contain pigments or dyes, viscosity modifying additives and antioxidants, Generally the vehicle (urea- or urethane-amide) will make up 50–95% by weight, especially 75–95% by weight of any ink, with viscosity modifying additives making up the bulk of the remainder and other additives, such as antioxidants, pigments, dyes, etc. in small amounts to make up the balance, e.g. typically less than 10% by weight of the total formulation.

Materials which may typically be used to modify the viscosity of inks containing the urea- or urethane-amides are; stearone, carnauba wax, stearyl stearamide, hydrogenated castor oil and erucamide.

The compatibility of the materials with dye stuffs and pigments must be determined by experimentation, but most of the colorants commonly used in ink jet applications are suitable.

The present invention will now be explained in more detail by way of the following non-limiting examples.

EXAMPLE 1

An amine functional amide material was prepared by reacting one mole of ethylene diamine with one mole of stearic acid. When fully processed this amide material had an acid value of 2.5 mg KOH/g and an amine value of 69.5 mg KOH/g. The ball and ring melting point of the material was 128° C. and it had a viscosity of <10 centipoise at 150° C. This material was designated amide 1.

EXAMPLE 2

An amine functional amide material was prepared by one mole of ethylene diamine with one mole of 3,5,5-trimethylhexanoic acid. The resulting amide material had a ball and ring melting point of 52° C. and a viscosity of <10 centipoise at 125° C. The acid value of the material was 4.2 mg KOH/g and its amine value was 125.4 mg KOH/g. This material was designated amide 2.

EXAMPLE 3

An amine functional amide material was prepared by reacting one mole of isophorone diamine with one mole of stearic acid. The resultant solid had an acid value of 1.2 mg KOH/g and an amine value of 117.0 mg KOH/g. Its melting point by the ball and ring method was 61° C. and at 125° C. its viscosity was less than 10 centipoise. This material was designated amide 3.

EXAMPLE 4

A hydroxy functional amide material was prepared by reacting one mole of ethylene diamine with one of 12-hydroxystearic acid and one mole of 3,5,5-trimethylhexanoic acid. The opaque solid produced had a hydroxy value of 109.1 mg KOH/g, an acid value of 7.5 mg KOH/g and an amine value of 9.0 mg KOH/g. The diamide had a ball and ring melting point of 129° C. and a viscosity at 125° C. of 50 centipoise. This material was designated amide 4.

EXAMPLE 5

Trimethylhexamethylene diisocyanate (1 mole) was charged to a round bottomed reaction flask fitted with a stirrer, a thermometer and an inert gas (nitrogen) sparge line. The material was heated to 60° C. and amide 1 (2 moles) added carefully to it, such that the temperature of the resultant exotherm did not climb above 100° C. When all of the amide had been added and no further exotherm was observed, the reaction was heated to 150° C. and held until the free isocyanate content of the urea-amide formed was below 30 ppm (as determined by titration and IR analysis).

This reaction yielded an opaque solid urea-amide with a ball and ring melting point of 128° C., a softening point of 136° C. (as determined by differential scanning calorimetry) and a viscosity of less than 10 centipoise at 150° C.

EXAMPLE 6

Octadecyl isocyanate (1 mole) was charged into a flask and was heated with stirring and under an inert atmosphere to 85° C. Amide 2 (1 mole) was then carefully added in powdered form at a rate which prevented the resultant exotherm from climbing about 100° C. Once all the amide had been added and the exotherm had abated, the reaction was driven to completion by heating it to 160° C.

This reaction produced an urea-amide material with a ball and ring melting point of 94° C., a DSC determined softening point of 73.4° C., a free isocyanate content below 30 ppm and a viscosity of 30 centipoise at 125° C.

EXAMPLE 7

Octadecyl isocyanate (1 mole) was charged to a flask and heated to 60° C. with stirring and under an inert atmosphere. Amide 3 (1 mole) was carefully added to the reaction flask at a rate such that the temperature of reaction did not climb above 100° C. When the reaction no longer exothermed, it was heated up to 150° C and controlled at this temperature until the free isocyanate value had dropped down below 30 ppm.

The batch was then cooled and discharged to yield a translucent, solid urea-amide with a ball and ring melting point of 63° C., a DSC determined softening point of 43° C. and a viscosity of 220 centipoise at 125° C.

EXAMPLE 8

Trimethylhexamethylene isocyanate (1 mole) and octadecyl isocyanate (1 mole) were charged to a heated flask and heated under a nitrogen atmosphere and under stirring to 65°

C. Amide 4 (3 moles) was then carefully added to the mixture of isocyanates, ensuring that the reaction temperature did not climb above 100° C. Once all the amide had been added and all exotherming had ceased, the batch was slowly heated up to 160° C. and held at this temperature until the isocyanate content had dropped below 30 ppm.

The resulting solid urethane-amide was a clear material with a ball and ring melting point of 95° C., a DSC determined softening point of 71° C. and a viscosity of 150 centipoise at 125° C.

What is claimed is:

1. A urea-amide or urethane-amide material suitable for use in a hot melt ink, the material having a melting point greater than 65° C. and being obtained by reacting a mono- or diisocyanate with one or more functional amide materials which are the reaction products of:
    (a) (i) one or more hydroxy functional primary or secondary arnines; or
       (ii) one or more diprimary diamines; or
       (iii) a mixture of components (i) and (ii); and
    (b) a monofunctional carboxylic acid, a difunctional carboxylic acid or a hydroxy carboxylic acid or a mixture of any two or more thereof.

2. A material according to claim 1, wherein functional amide material(s) is or are selected from:
    (i) the reaction product of one equivalent of a diprimary diamine component with one equivalent of a monocarboxylic acid or hydroxy functional monocarboxylic acid;
    (ii) the reaction product of one equivalent of a diprimary diamine component with one equivalent of a monocarboxylic acid;
    (iii) the reaction product of one equivalent of a primary monoamine with hydroxy functionality, with one equivalent of a monocarboxylic acid; or
    (iv) the reaction products (i) or (ii), but where an equivalent of acid functionality is made up of a proportion of monocarboxylic acid, dicarboxylic acid and/or hydroxy functional monocarboxylic acids.

3. A material according to claim 1, wherein the functional amide has hydroxy functionality and the resultant material is a urethane compound.

4. A material according to claim 1, wherein the functional amide has amine functionality and the resultant material is a urea compound.

5. A material according to claim 1, wherein the mono- or diisocyanate is aliphatic.

6. A material according to claim 4, wherein the mono- or diisocyanate is selected from isophorone diisocyanate, trimethylhexamethylene diisocyanate and octadecyl monoisocyanate.

7. A material according to claim 1, wherein the at least one said functional amide material is produced from a diprimary diamine selected from ethylene diamine, neopentane diamine, 2,4,4-trimethylhexandiamine, 2-butyl-2-ethyl 1,5 pentane diamine, 1,3-diaminopentane, isophorone diamine and 2 methyl 1,5 pentamethylene diamene.

8. A material according to claim 1, wherein the at least one said functional amide material is produced from a hydroxy-functional primary or secondary amine selected from ethanolamine, diethanolamine and n-methyl diethanolamine.

9. A material according to claim 1, wherein the at least one said functional amide material is produced from a mono-functional carboxylic acid selected from stearic acid, acetic acid, 3,5,5-trimethylhexanoic acid, decanoic acid, propanoic acid, 2,2 dimethylpropionic acid, isooctanoic acid, isoheptanoic acid, isobutyric acid and isodecanoic acid.

10. A material according to claim 1, wherein the at least one said functional amide material is produced from a hydroxy carboxylic acid selected from 12-hydroxy stearic acid, 12-hydroxydodecanoic acid, 2-hydroxyhexanoic acid, 16-hydroxyhecadecanoic acid and 2-hydroxyisobutyric acid.

11. A material according to claim 1, wherein the functional amide material has a melting point greater than 50° C. and a viscosity less than 200 centipoise at 125° C.

12. A material according to claim 1, having an average molecular weight of from 400 to 2000.

13. A hot melt ink comprising a colourant and a material according to claim 1.

14. A hot melt ink according to claim 13, further comprising a viscosity modifier.

15. A material according to claim 1, wherein the material is obtained by reacting the mono- or diisocyanate with an at least stoichiometric amount of the one or more functional amide materials.

16. A material according to claim 1, wherein the material obtained by reacting the mono- or diisocyanate with the one or more functional amide materials has a free isocyanate content below 30 ppm.

17. A material according to claim 1, wherein the material is obtained by reacting the mono- or diisocyanate with the one or more functional amide materials, an exothermic portion of the reaction being maintained at a temperature below 100° C.

* * * * *